(12) United States Patent
Pathak et al.

(10) Patent No.: US 10,583,061 B2
(45) Date of Patent: Mar. 10, 2020

(54) TILT COMPENSATION FOR TREMOR CANCELLATION DEVICE

(71) Applicant: Verily Life Sciences LLC, Mountain View, CA (US)

(72) Inventors: Anupam Pathak, Mountain View, CA (US); Dylan Owens, Sunnyvale, CA (US)

(73) Assignee: VERILY LIFE SCIENCES LLC, South San Francisco, CA (US)

( * ) Notice: Subject to any disclaimer, the term of this patent is extended or adjusted under 35 U.S.C. 154(b) by 254 days.

(21) Appl. No.: 15/257,111

(22) Filed: Sep. 6, 2016

(65) Prior Publication Data

US 2018/0064597 A1 Mar. 8, 2018

(51) Int. Cl.
| | | |
|---|---|---|
| *A61H 1/00* | (2006.01) | |
| *A61F 2/54* | (2006.01) | |
| *G05B 15/02* | (2006.01) | |
| *A61B 5/11* | (2006.01) | |
| *A61B 5/00* | (2006.01) | |

(Continued)

(52) U.S. Cl.
CPC ............. *A61H 1/008* (2013.01); *A47G 21/02* (2013.01); *A61B 5/1101* (2013.01); *A61B 5/4836* (2013.01); *A61F 2/54* (2013.01); *G05B 15/02* (2013.01); *A47G 21/04* (2013.01); *A47G 2200/046* (2013.01)

(58) Field of Classification Search
CPC ........... A61H 1/008; A61F 2/54; G05B 15/02; A47G 21/04; A47G 2200/046; A47G 21/02; A61B 5/1101; A61B 5/4836
See application file for complete search history.

(56) References Cited

U.S. PATENT DOCUMENTS 8,308,664 B2 * 11/2012 Pathak ..................... G03B 5/00
600/595
2004/0096368 A1 * 5/2004 Davis .................... B01L 3/0293
422/400

(Continued)

FOREIGN PATENT DOCUMENTS

WO 2013/049020 A1 4/2013
WO 2016/133621 A1 8/2016

OTHER PUBLICATIONS

International Search Report and Written Opinion from the International Searching Authority dated Nov. 30, 2017, for International Application No. PCT/US2017/049146, filed Aug. 29, 2017, 11 pages.

(Continued)

*Primary Examiner* — Lynsey C Eiseman
*Assistant Examiner* — Jessandra F Hough
(74) *Attorney, Agent, or Firm* — Christensen O'Connor Johnson Kindness PLLC

(57) ABSTRACT

A method of tremor reduction in a handheld device includes measuring a tremor motion and a tilt motion with a motion tracking module ("MTM") disposed in a housing of the handheld device. In response to measuring the tremor motion, an attachment arm is moved with at least one motion generating mechanism to reduce the tremor motion in the attachment arm. Additionally, in response to measuring the tilt motion, the attachment arm is moved with the at least one motion generating mechanism to resist the attachment arm hitting a hard stop in the handheld device.

23 Claims, 5 Drawing Sheets

(51) Int. Cl.
A47G 21/02 (2006.01)
A47G 21/04 (2006.01)

(56) References Cited

U.S. PATENT DOCUMENTS

| | | | | |
|---|---|---|---|---|
| 2007/0050139 | A1* | 3/2007 | Sidman | F16M 11/041 |
| | | | | 318/649 |
| 2014/0052275 | A1* | 2/2014 | Pathak | A61F 4/00 |
| | | | | 623/65 |
| 2014/0303660 | A1* | 10/2014 | Boyden | A61B 17/32 |
| | | | | 606/170 |
| 2016/0121110 | A1* | 5/2016 | Kent | A61N 1/36139 |
| | | | | 607/45 |
| 2017/0020704 | A1* | 1/2017 | Wu | A61F 4/00 |

OTHER PUBLICATIONS

Ang, W. T., et al.—Design of All-Accelerometer Inertial Measurement Unit for Tremor Sensing in Hand-held Microsurgical Instrument, Research Showcase @ CMU, 2003, 7 pages.

* cited by examiner

TILT COMPENSATION FOR TREMOR CANCELLATION DEVICE

TECHNICAL FIELD

This disclosure relates generally to unintentional muscle movements, and in particular but not exclusively, relates to stabilizing a handheld tool while it is being used by the user.

BACKGROUND INFORMATION

Movement disorders are often caused by chronic neurodegenerative diseases such as Parkinson's Disease ("PD") and Essential Tremor ("ET"). Both of these conditions are currently incurable and cause unintentional muscle movements or human tremors—uncontrollable rhythmic oscillatory movements of the human body. In many cases human tremors can be severe enough to cause a significant degradation in quality of life, interfering with daily activities/tasks such as eating, drinking, or writing.

Currently, persons with chronic neurodegenerative diseases are typically medicated with drugs that vary in effectiveness. The alternative to pharmacological treatment is brain surgery, such as deep brain stimulation (DBS) surgery. Similar to pharmacological treatments, DBS surgery varies in its effectiveness while being invasive and dangerous. Both forms of treatment are therefore non-optimal for treating persons with chronic neurodegenerative diseases, especially with respect to performing daily activities.

BRIEF DESCRIPTION OF THE DRAWINGS

Non-limiting and non-exhaustive embodiments of the invention are described with reference to the following figures, wherein like reference numerals refer to like parts throughout the various views unless otherwise specified. The drawings are not necessarily to scale, emphasis instead being placed upon illustrating the principles being described.

DETAILED DESCRIPTION

Embodiments of an apparatus and method for tilt compensation for a tremor cancellation device are described herein. In the following description numerous specific details are set forth to provide a thorough understanding of the embodiments. One skilled in the relevant art will recognize, however, that the techniques described herein can be practiced without one or more of the specific details, or with other methods, components, materials, etc. In other instances, well-known structures, materials, or operations are not shown or described in detail to avoid obscuring certain aspects.

Reference throughout this specification to "one embodiment" or "an embodiment" means that a particular feature, structure, or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

Handheld devices may be used to counteract tremor resulting from Parkinson's or other diseases. For example, a handheld device with a spoon attachment may allow a person with Parkinson's to eat normally by stabilizing the spoon end of the device so that food stays on the spoon. While the handheld device may effectively counter tremor motion by filtering high-frequency motions, it may not respond well to tilt (low-frequency) motions that result from the attachment end of the device being pulled by gravity. These tilt motions may result in the attachment end of the device hitting a hard stop. In the spoon example, if the attachment end of the device hits a hard stop (e.g., the outermost point of its range of motion) the food on the spoon may be thrown off of the spoon. In other words, tilting the device side to side my result in the spoon attachment falling against one of the device's hard stops. Accordingly, systems and methods here both mitigate tremor motions in handheld devices and also prevent low frequency tilt motions from limiting usability.

Figure 1A:
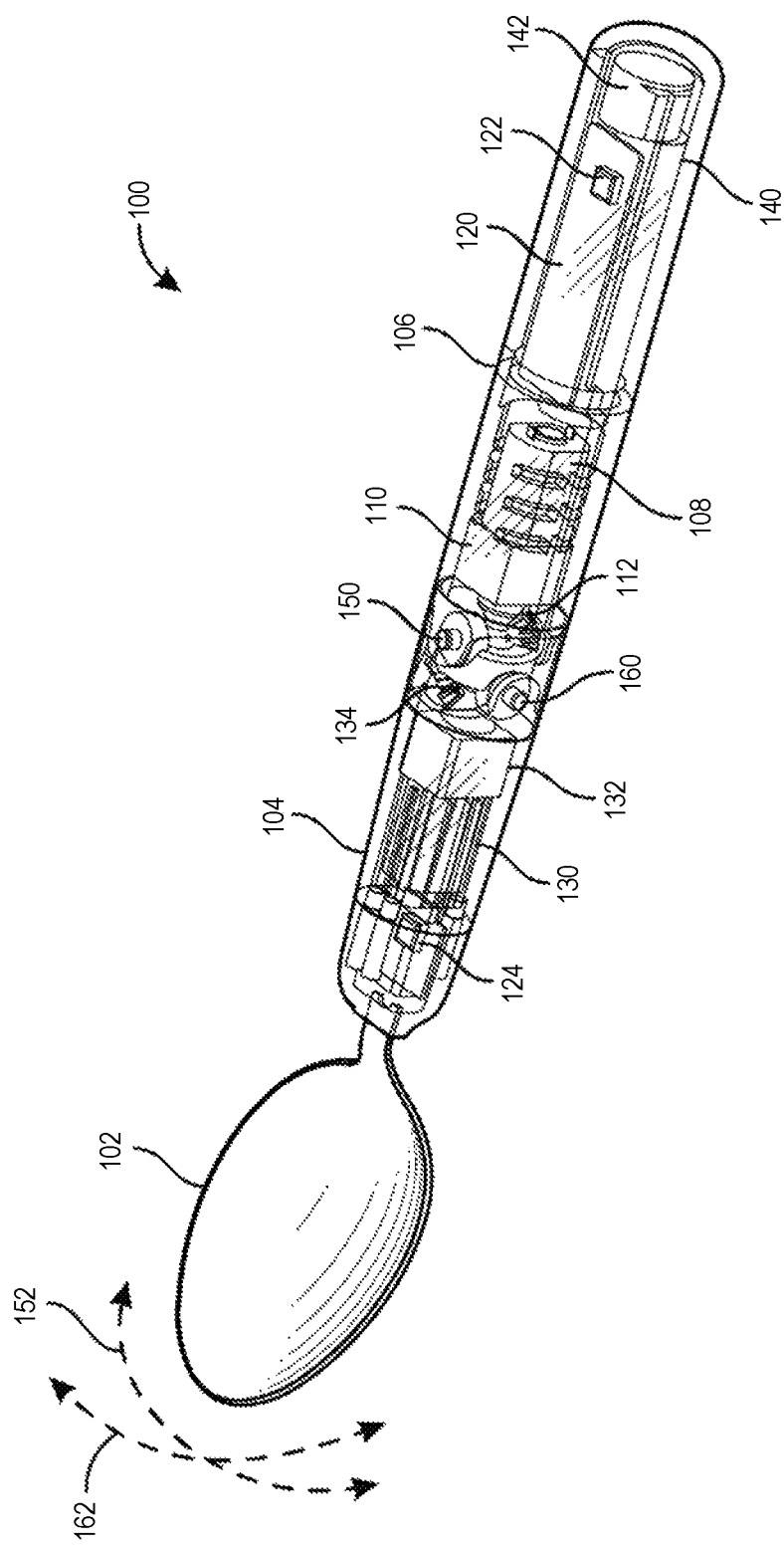
FIG. 1A illustrates a handheld tool that tracks unintentional muscle movements and performs motion stabilization, in accordance with an embodiment of the disclosure.

FIG. 1A illustrates a handheld tool 100 that tracks unintentional muscle movements and performs motion stabilization, in accordance with an embodiment of the disclosure. Handheld tool 100 is capable of detecting and compensating for unintentional high frequency muscle movement (e.g., tremors) and low frequency motions (e.g., tilts). In one embodiment, the muscle movements are high frequency when they occur in a range of approximately 1-2 centimeters about a central point of handheld tool 100, although unintentional high frequency muscle movements may be as large as 8-10 centimeters about a central point of handheld tool 100. In the embodiments discussed herein, handheld tool 100 tracks these unintentional high frequency muscle movements, and stabilizes a position of attachment arm 104 in spite of the unintentional muscle movements while implement 102 is being used by a user. Moreover, circuitry in handheld tool 100 may detect when handheld tool 100 is being slowly tilted, and may prevent attachment arm 104 from hitting one of the sidewalls causing a hard stop.

Accordingly, the illustrated embodiment of handheld tool 100 includes motion tracking module ("MTM") 120 for measuring and tracking user tremors as well as low frequency tilt motions. In one embodiment, handheld tool 100 includes two or more sensors (e.g., sensor 122 and 124) for providing signals to MTM 120 for compensating for tremors and tilt motions, as discussed herein. These subsystems may have distinct components, or share some components such as power systems, memory, and may even share one or more sensors.

Handheld tool 100 includes housing 106, which functions as a handle enabling a user to hold handheld tool 100. As stated, handheld tool 100 also includes attachment arm 104 coupled to housing 106 via motion generating mechanisms, as discussed in greater detail below. Attachment arm 104 is configured to accept an attachment 102 (e.g., a user-assistive device, such as a spoon, fork, toothbrush, paintbrush, or the like) to its end distal from housing 106. In one embodiment, attachment arm 104 is integrated with a specific type of implement 102 (e.g., the spoon as illustrated). In other embodiments, attachment arm 104 can receive a variety of different implements 102 in a variety of ways including but not limited to friction hold, snap clasp, magnet, screw, or other form of locking mechanism (see e.g., FIGS. 1B and 2A-2C).

The depicted embodiment of handheld tool 100 includes motion tracking module 120 for measuring and tracking tremors, such as unintentional high frequency muscle movements of a user, as well as for controlling stabilization performed by handheld tool 100 using a first motion generating mechanism (e.g., first actuator 108, first gear reduction unit 110, and first gearing unit 112) and a second motion generating mechanism (e.g., second actuator 130, second gear reduction unit 132, and second gearing unit 134), discussed in greater detail below. In one or more embodiments, first actuator 108 and second actuator 130 may include motors. One skilled in the art will appreciate that while the depicted embodiment has two motion generating mechanisms other embodiments may have one or more than two. In several embodiments, attachment arm 104 is coupled with housing 106 via the coupling of the first motion generating mechanism with the second motion generating mechanism. Furthermore, one or more components of MTM 120 are rigidly attached to housing 106 to measure and track tremors of the handle that the user holds. FIG. 1A illustrates MTM 120 as a single component within housing 106; however, in other embodiments, MTM 120 includes several functional items that may assume a variety of different form factors and may further be spread throughout housing 106, such as within attachment arm 104. In one embodiment, MTM 120 includes at least one gyroscope, and the at least one gyroscope is located in at least one of a distal end of attachment arm 104 or anywhere in the housing 106.

The illustrated embodiment of handheld tool 100 further includes at least two motion sensors (e.g., a first motion sensor 122 placed along or within body and a second motion sensor 124 placed along or within attachment arm 104). The motion sensors 122 and 124 respectively measure movements of housing 106 and attachment arm 104, to enable MTM 120 to determine movements of housing 106 and attachment arm 104 relative to one another. The sensor 122 sends motion signals back to MTM 120 so that MTM 120 can determine, in real time or near real time, direction, speed, and magnitude of unintentional high frequency muscle movements of a user using handheld tool 100. These measured movements are provided to MTM 120 to enable a controller disposed in MTM 120 to provide motion signals that drive the first and second motion generating mechanisms to stabilize the implement 102 despite the user's unintentional high frequency muscle movements. In one embodiment, the motion sensors 122 and 124 are sensors including, but not limited to, one or more of an accelerometer, gyroscope, or combination of the two. In another embodiment, each of motion sensor 122 and 124 is a inertial measuring unit.

Handheld tool 100 further includes a portable power source 140 to power the MTM 120, actuator 108, and actuator 130. The portable power source 140 can include one or more rechargeable batteries. In embodiments, the rechargeable batteries of portable power source 140 may be recharged via charging interface 142 to a charging power source, where charging interface 142 couples portable power source 140 to the charging power source via an indicative, wired, or other form of connection. Furthermore, power source 140 may utilize other options including but not limited to a solar panel, primary batteries, etc.

In one embodiment, the first motion sensor 122 and second motion sensor 124 are inertial motion sensors respectively distributed in housing 106 and attachment arm 104. In one embodiment, the first motion sensor 122 is responsible for measuring movements of the housing 106 and the second motion sensor 124 is responsible for measuring movements of the attachment arm 104. The first and second motion sensors 122 and 124 provide motion signals, indicative of the measured movements, to MTM 120 for determining the motion of the housing 106 as well as the relative motions of the housing 106 and the attachment arm 104. In embodiments, one or more of the components for tracking tremor motions and/or performing tilt stabilization may be omitted and/or positions of sensors changed while still implementing the tremor tracking and tilt stabilization functionality disclosed herein. As examples, rotary encoders, potentiometers, or other position tracking devices placed on the joints of movement of the handheld tool 100, and a single motion sensor can be employed either in the tip (e.g., attachment arm 104 or implement 102) or housing 106. In these embodiments, the combination of sensors and placement on handheld tool 100 enable MTM 120 to infer (through device kinematics) where attachment arm 104 and housing 106 are, and their positions relative to each other, for tremor tracking and tilt compensation purposes.

The first motion sensor 122 and second motion sensor 124 detect unintentional muscle movements and measure signals related to these unintentional muscle movements that are created when a user adversely affects motion of implement 102 (e.g., as a result of unintentional high frequency muscle movements). These sensors also detect the motion of the stabilized output relative to the housing 106. In one embodiment, the first motion sensor 122 detects movements of the housing 106, although sensor 124 could also be used for detecting movements of the housing 106. Furthermore, the combined measurements of the sensors 122 and 124 enable movements of the housing 106 and implement 102 relative to one another to also be detected. The controller coupled to, or included in, MTM 120 sends voltage commands in response to the detected motions to at least one of actuator 108 and actuator 130. The voltage commands are chosen by the controller to generate a complementary motion to the detected motions of housing 106. In one embodiment, the complementary motion is a positioning of attachment arm 104 upon jointly driving actuator 108 and actuator 130 to stabilize implement 102 (e.g., maintain implement 102 in a centered position relative to the user's tremors or unintentional muscle movements effecting motion of the housing 106). The voltage commands drive one or more of actuator 108 and actuator 130 to generate motion of the attachment arm 104 and therefore the implement 102 in a direction opposite to the detected user motions. Furthermore, the voltage commands further drive one or more of actuator 108 and actuator 130 to generate a motion of equal magnitude of the detected user motion. The voltage commands from the controller in MTM 120 therefore control motion of the implement 102 by jointly driving the motion generating mechanisms to cancel out the user's unintentional high frequency motion thereby stabilizing the implement 102 relative to motion of the housing 106 by a user.

Further the controller in MTM 120 may, in response to MTM 120 detecting a tilt motion, control the at least one motion generating mechanism to resist attachment arm 104 hitting a hard stop in handheld tool 100. To keep attachment arm 104 from hitting the hard stop, motion sensors 122 and 124 in MTM 120 may use an accelerometer to measure high frequency motion corresponding to the tremor motion and low frequency motion corresponding to the tilt motion. MTM 120 (or the controller) may apply least one of a low pass filter or a high pass filter to distinguish between the tremor motion and the tilt motion. In embodiments where a high pass filter is used, the position of the attachment arm 104 set point may shift in the controller. In one embodiment, the set point is the location in the attachment arm's 104 range of motion that attachment arm 104 is trying to get to. The controller/MTM 120 may flip between controlling high frequency (tremor motion) and low frequency (tilt) motion and send instructions to the at least one motion generating mechanism to oppose the low frequency motion and resist attachment arm 104 hitting the hard stop. Alternatively, the controller/MTM 120 may control the tremor motion and tilt motion in parallel. This may include matching the motor (included in the motion generating mechanism) constant to the inertia of the handheld device at high frequencies, and matching the motor constant to the torque of gravity at low frequencies.

In embodiments where MTM 120 includes both an accelerometer and a gyroscope, the accelerometer and the gyroscope may detect an orientation of handheld tool 100 including a pitch of handheld tool 100 and a roll of the handheld tool 100 to resist attachment arm 104 hitting a hard stop. For example, if the handheld tool 100 is rolled to the side, a low frequency gain may be applied to the motor to produce the torque equal and opposite to the gravitational vector (cosine of the angle from the zero plane). This low frequency gain is added to any high-frequency tremor correction signals to still produce tremor compensation properties. The controller may employ at least one of a Kalman filter or a complementary filter, and in response to detecting the tilt motion, the controller may produce torque in the attachment arm 104 equal and opposite to a gravitational vector. Generally, Kalman filters use an iterative two-step process: the first step is a prediction step where the filter estimates the current state of variables (here position, velocity, etc. of attachment arm 104); the second step involves measuring the actual state and updating the current state estimation with a weighted average (with more weight being given to parameters with higher certainty). A complementary filter is a frequency domain filter using two or more complementary transfer functions to construct a noise-free signal.

In one embodiment, the handheld tool 100 includes a first motion generating mechanism having the first actuator 108, first gear reduction unit 110, and first gearing unit 112. In response to a first set of voltage commands from the controller in MTM 120, the first actuator 108 drives the first gearing unit 112 through the first gear reduction unit 112 to move the attachment arm 104 and the attached implement 102 on pivot 150 in a first degree of freedom 152 relative to the housing 106. Similarly, in response to a second set of voltage commands from the controller in MTM 120, the second actuator 130 drives the second gearing unit 134 through the second gear reduction unit 132 to move the attachment arm 104 and the attached implement 102 on pivot 160 in a second degree of freedom 162 relative to the housing 106. The first degree of freedom and the second degree of freedom are different, and in one embodiment, the first and second degrees of freedom are perpendicular to one another (e.g., 90 degrees different from one another). In embodiments, the first and/or second motion generating mechanisms employ gearing units that translate motion to orthogonal directions relative to the motions generated by their respective actuators. Such a translation of motion of the actuators to an orthogonal direction can be achieved through bevel gearing units, such as those illustrated in FIGS. 1A-1B. Other types of gearing or combinations of types of gearing, such as work gearing units, a work gearing unit and a bevel gearing unit, etc., capable of translating the actuators' 108 and 130 motions to orthogonal directions can be employed by the handheld tool 100 consistent with the discussion herein. All of these configurations may be used to cancel tremor and compensate for tilt motion in accordance with the teachings of the present disclosure.

Figure 1B:
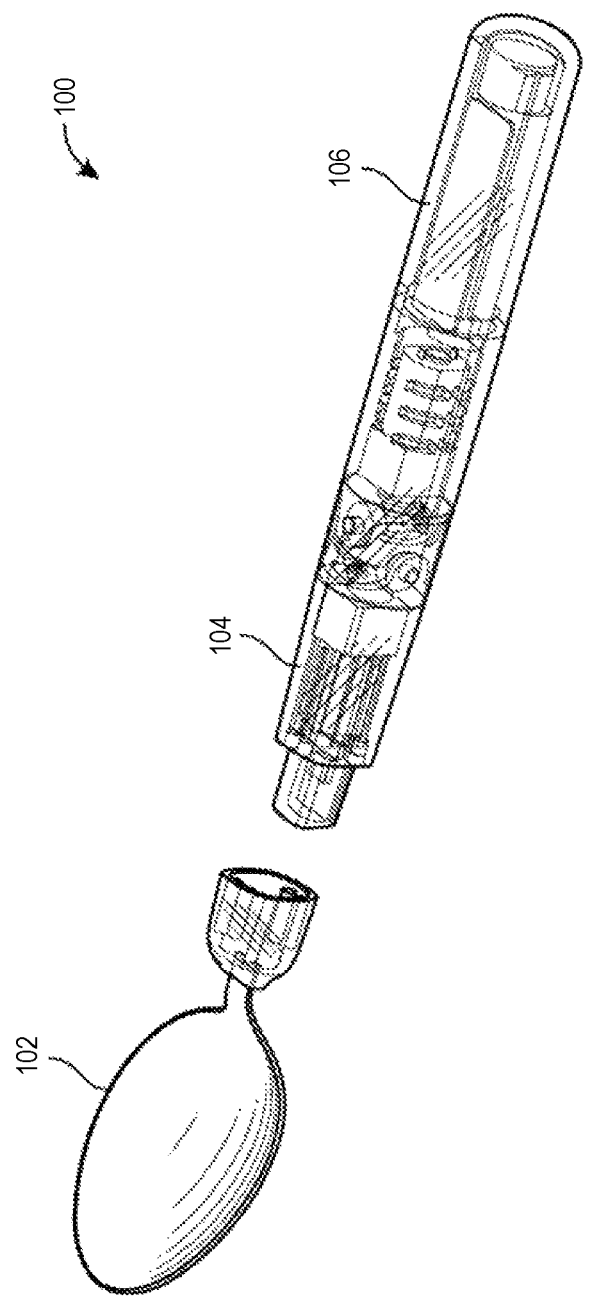
FIG. 1B illustrates the handheld tool of FIG. 1 and further shows attachment/detachment functionality, in accordance with an embodiment of the disclosure.

FIG. 1B illustrates handheld tool 100 of FIG. 1 and further shows attachment/detachment functionality, in accordance with an embodiment of the disclosure. As shown, the tool/implement 102 (spoon) is detachable from attachment arm 104. In one embodiment the attachment arm 104 and implement 102 may click together, be held together by magnetic force, screw together, or the like. One skilled in the art will appreciate that there are many different ways to attach implement 102 to attachment arm 104 to make it easily removable but keep it from falling off during use. This functionality allows the user of handheld tool 100 to use a variety of implements. In one embodiment, handheld tool 100 may recognize the type of implement 102 attached to attachment arm 104 and adjust the algorithms used to stabilize the tool accordingly. Alternatively a user may annually adjust the stabilization (tremor and tilt) algorithms depending on the type of implement 102. For example the user, or handheld tool 100, may adjust the resistance handheld tool 100 outputs to prevent attachment arm 104 from hitting a hard stop, depending on the type of implement 102 being used.

Figure 1C:
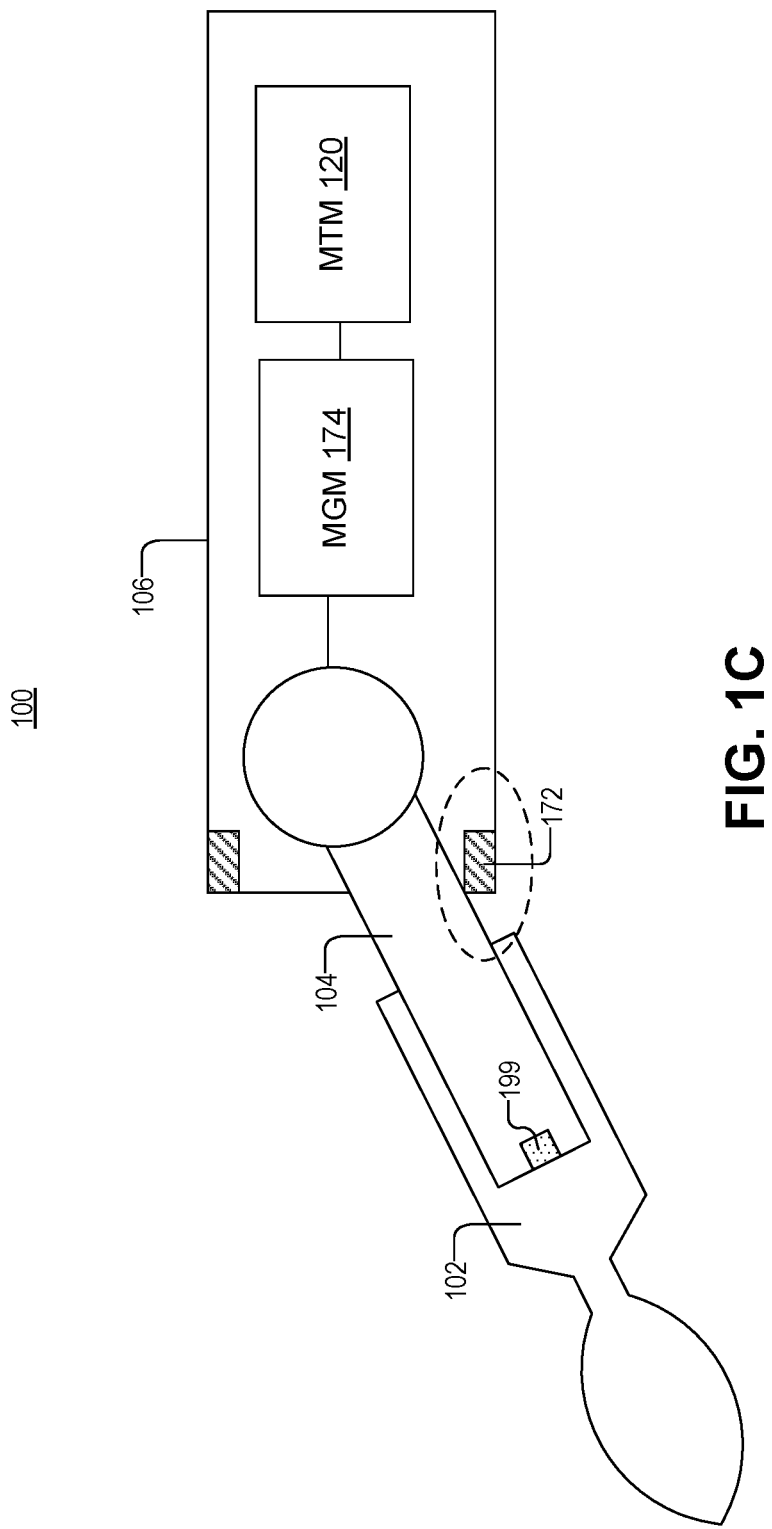
FIG. 1C illustrates the handheld tool of FIG. 1 along with one example of a hard-stop, in accordance with an embodiment of the disclosure.

FIG. 1C illustrates handheld tool 100 of FIG. 1 along with one example of a hard-stop, in accordance with an embodiment of the disclosure. One skilled in the art will appreciate that the diagram is highly simplified to avoid obscuring certain aspects of the disclosure. As shown, attachment arm 104 has run into bumper 172 which is one example of a hard stop. However, one skilled in the art will appreciate that a hard stop need not necessarily be physical; for example a hard stop may be programmed into the device to prevent it from damage. When the attachment arm 104 runs into bumper 172 it causes the attachment arm (and implement 102) to come to an abrupt jolted stop. This may cause food on implement 102 to fly off, or may even cause the user to hurt themselves if the implement is in the user's mouth. Accordingly, it is desirable for handheld tool 100 to resist hitting the hard stop, and ensure that a gradual increase in resistance is applied to attachment arm 104 prior to it reaching the hard stop. This resistance may be applied by motion generating mechanism 174. It is worth noting that handheld tool 100 may still occasionally hit the hard stop if enough force is applied to attachment arm 104 (as depicted); however, handheld tool 100 will resist this motion and will also resist tilting motions which may otherwise result in attachment arm 104 hitting the hard stop.

In the depicted embodiment MTM 120 includes at least one gyroscope 199 located in the distal end of attachment arm 104. It is worth noting that although gyroscope is located outside of the boundaries of the MTM 120 block, any device used for measuring motion may be considered "included" in MTM 120 regardless of its location in handheld tool 100. Moreover, in one or more embodiments, MTM 120 may include a commercially available or proprietary internal measurement unit (IMU).

Figure 2A:
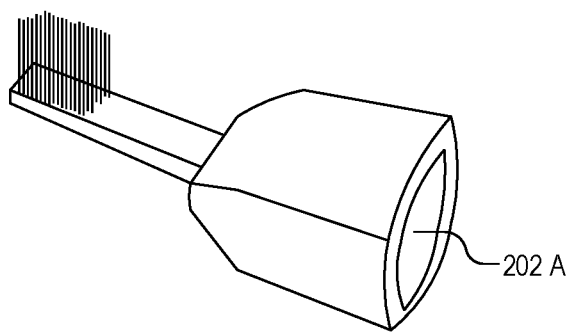
FIGS. 2A-2C illustrate a variety of handheld tool attachments, in accordance with several embodiments of the disclosure.
Figure 2B:
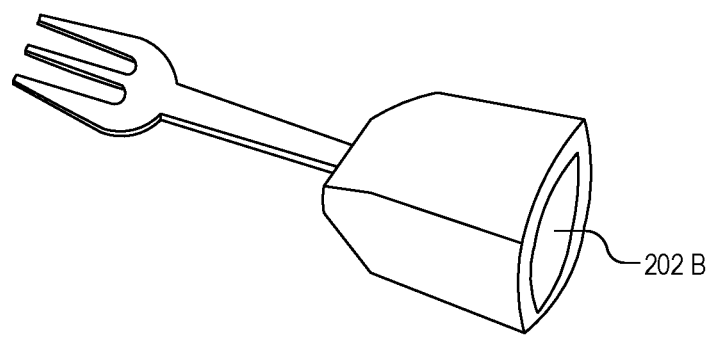
Figure 2C:
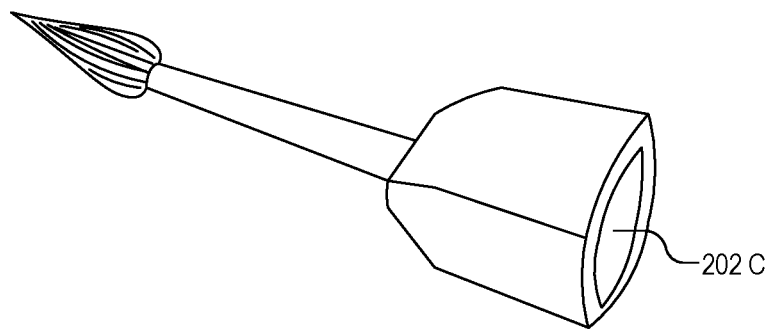

FIGS. 2A-2C illustrate a variety of handheld tool attachments, in accordance with several embodiments of the disclosure. One skilled in the art will appreciate that the tool attachments depicted are not exhaustive and that other tool attachments may be used.

FIG. 2A shows toothbrush attachment 202A that is compatible with the handheld tool (e.g., handheld tool 100) of FIG. 1A. The toothbrush may allow a person with tremor to brush their teeth without injuring the interior of their mouth by inadvertently jamming the toothbrush into their teeth/gums. Toothbrush attachment 202A may be preferably used with a handheld tool that resists contacting hard stops. Because some pressure is necessarily applied to toothbrush tool 202A, the device should resist hitting a hard stop to keep the user from injuring themselves.

FIG. 2B illustrates fork attachment 202B. Similar to toothbrush attachment 202A, it may be advantageous to use the fork in conjunction with a handheld tool that has hard stop resistance; this keeps the user from inadvertently injuring themselves by having the movement of the attachment arm max out FIG. 2C depicts paintbrush attachment 202C. Although encountering a hard stop with a paintbrush attachment poses little risk for the user of the handheld tool, a hard stop may result in a painting that has abrupt transitions between lines and lacks aesthetic appeal. Accordingly, it may be advantageous to use paintbrush attachment 202C with a handheld tool that resists the effects of hard stops.

It is worth noting that the devices depicted here may all have their own specific tremor reduction and hard stop resistance hardware and algorithms. For instance, when using toothbrush attachment 202A, intricacy of movement may be less important than the ability to exert force. Accordingly, the resistance the attachment arm outputs to counteract encountering a hard stop may be relatively large. Conversely, in the case of paintbrush attachment 202C intricacy of movement may be prized over the force needed to effectively use the attachment. Accordingly, the handheld device may resist hitting the hard stop less with paintbrush attachment 202C than with toothbrush attachment 202A and fork attachment 202B.

Figure 3:
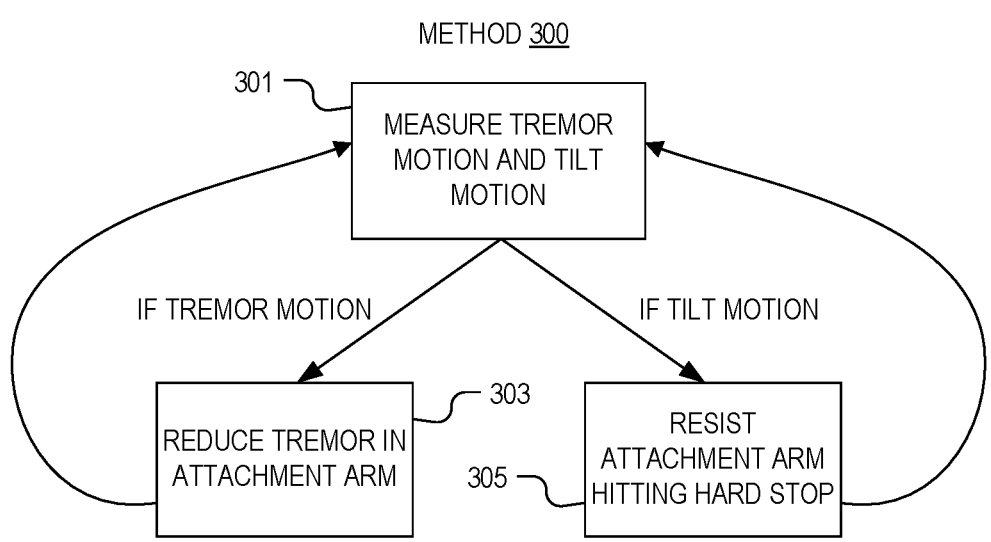
FIG. 3 is a flowchart illustrating a method of tremor stabilization and hard stop resistance, in accordance with several embodiments of the disclosure.

FIG. 3 is a flowchart illustrating a method 300 of tremor stabilization and hard stop resistance, in accordance with several embodiments of the disclosure. The order in which some or all of process blocks 301-305 appear in method 300 should not be deemed limiting. Rather, one of ordinary skill in the art having the benefit of the present disclosure will understand that some of method 300 may be executed in a variety of orders not illustrated, or even in parallel.

Block 301 illustrates measuring a tremor motion and a tilt motion with a motion tracking module ("MTM") disposed in a housing of the handheld device (e.g., handheld tool 100 of FIG. 1). Measuring the tremor motion and the tilt motion may include separating high frequency motion corresponding to the tremor motion from low frequency motion corresponding to the tilt motion and in response. In one embodiment, the tremor motion and the tilt motion may both be measured by an accelerometer, and at least one of a low pass filter or a high pass filter is used to distinguish between the tremor motion and the tilt motion. In another embodiment, measuring the tremor motion and the tilt motion includes using an accelerometer and a gyroscope included in the MTM, and the tremor motion and the tilt motion are separated using at least one of a Kalman filter or a complementary filter.

Block 303 illustrates moving the attachment arm to reduce tremor in the attachment arm. In one embodiment, the at least one motion generating mechanism included in the handheld device has a motor, and the motor output is adjusted to counteract the inertia of the housing using the attachment arm. This reduces the effect of the user's tremor in the attachment arm, and stabilizes the location of the distal end of the attachment arm.

Block 305 shows the handheld device resisting the attachment arm hitting a hard stop in response to measuring a tilt motion. As discussed above, the "hard stop" is a maximum movement distance in one direction; this may be either a physical limit or a limit built into software (e.g., a movement limit programmed into the device to prevent damage to the device).

In one embodiment, a motion generating mechanism disposed in the handheld tool resists the attachment arm hitting the hard stop in response to measuring the low frequency motion and shifting a set point of the attachment arm using the controller. In other words, the handled device shifts the location of the position that the attachment arm is trying to reach, when the handheld device realizes the attachment arm is too close to a hard stop. Further, resisting the attachment arm hitting the hard stop may include includes adjusting a motor output to counteract a torque of gravity resulting from the tilt motion. For example if the attachment arm starts to tilt and fall, the handheld device may detect this motion with an accelerometer/gyroscope and output a torque to counteract the fall. The torque may be equal and opposite to the gravitational vector.

The processes explained above are described in terms of computer software and hardware. The techniques described may constitute machine-executable instructions embodied within a tangible or non-transitory machine (e.g., computer) readable storage medium, that when executed by a machine will cause the machine to perform the operations described. Additionally, the processes may be embodied within hardware, such as an application specific integrated circuit ("ASIC") or otherwise.

A tangible non-transitory machine-readable storage medium includes any mechanism that provides (i.e., stores) information in a form accessible by a machine (e.g., a computer, network device, personal digital assistant, manufacturing tool, any device with a set of one or more processors, etc.). For example, a machine-readable storage medium includes recordable/non-recordable media (e.g., read only memory (ROM), random access memory (RAM), magnetic disk storage media, optical storage media, flash memory devices, etc.).

The above description of illustrated embodiments of the invention, including what is described in the Abstract, is not intended to be exhaustive or to limit the invention to the precise forms disclosed. While specific embodiments of, and examples for, the invention are described herein for illustrative purposes, various modifications are possible within the scope of the invention, as those skilled in the relevant art will recognize.

These modifications can be made to the invention in light of the above detailed description. The terms used in the following claims should not be construed to limit the invention to the specific embodiments disclosed in the specification. Rather, the scope of the invention is to be determined entirely by the following claims, which are to be construed in accordance with established doctrines of claim interpretation.

What is claimed is:

1. A method of tremor reduction in a handheld device, comprising:

measuring a tremor motion and a tilt motion about a pivot point with a motion tracking module ("MTM") disposed in a housing of the handheld device;

in response to measuring the tremor motion, moving an attachment arm with at least one motion generating mechanism to reduce the tremor motion in the attachment arm; and in response to measuring the tilt motion about the pivot point, moving the attachment arm with the at least one motion generating mechanism to resist the attachment arm hitting a hard stop programmed into or identified by the handheld device, wherein the hard stop is an outermost point in a range of portion of the attachment arm, wherein a resistance, created by the at least one motion generating mechanism, to the attachment arm increases as the attachment arm approaches the hardstop.

2. The method of claim 1, wherein measuring the tremor motion and the tilt motion includes separating high frequency motion corresponding to the tremor motion from low frequency motion corresponding to the tilt motion, and in response to measuring the low frequency motion resisting the attachment arm hitting the hard stop, wherein the hard stop is a maximum movement distance in one direction.

3. The method of claim 2, wherein measuring the tremor motion and the tilt motion includes:
measuring the tremor motion with an accelerometer;
measuring the tilt motion with the accelerometer; and
using at least one of a low pass filter or a high pass filter to distinguish between the tremor motion and the tilt motion, and wherein the at least one motion generating mechanism resists the attachment arm hitting the hard stop in response to measuring the low frequency motion and shifting a set point of the attachment arm.

4. The method of claim 3, wherein the at least one motion generating mechanism includes a motor, and wherein reducing the tremor motion in the attachment arm includes adjusting a motor output to counteract an inertia of the housing, and wherein resisting the attachment arm hitting the hard stop includes adjusting the motor output to counteract a torque of gravity resulting from the tilt motion.

5. The method of claim 2, wherein measuring the tremor motion and the tilt motion includes using an accelerometer and a gyroscope included in the MTM.

6. The method of claim 5, wherein measuring the tremor motion and the tilt motion includes using at least one of a Kalman filter or a complementary filter.

7. The method of claim 5, wherein the at least one motion generating mechanism includes a motor, and wherein in response to detecting the tilt motion with the accelerometer and the gyroscope, the motor outputs a torque equal and opposite to a gravitational vector to resist the attachment arm hitting the hard stop.

8. A non-transitory machine readable storage medium having instructions stored thereon, which when executed by a processing system, cause the processing system to perform a method comprising:
measuring a tremor motion and a tilt motion about a pivot point of a handheld device with a motion tracking module ("MTM");
in response to measuring the tremor motion, controlling an attachment arm with at least one motion generating mechanism to reduce the tremor motion in the attachment arm, wherein the at least one motion generating mechanism is coupled to the attachment arm included in the handheld device; and in response to measuring the tilt motion about the pivot point, controlling the attachment arm with the at least one motion generating mechanism to resist the attachment arm hitting a hard stop programmed into or identified by the handheld device, wherein the hard stop is an outermost point in a range of portion of the attachment arm, wherein a resistance, created by the at least one motion generating mechanism, to the attachment arm increases as the attachment arm approaches the hardstop.

9. The non-transitory machine readable storage medium of claim 8, wherein measuring the tremor motion and the tilt motion includes:
measuring high frequency motion corresponding to the tremor motion with an accelerometer included in the MTM;
measuring low frequency motion corresponding to the tilt motion with the accelerometer; and
using at least one of a low pass filter or a high pass filter to distinguish between the tremor motion and the tilt motion.

10. The non-transitory machine readable storage medium of claim 9, wherein resisting the attachment arm hitting the hard stop includes adjusting an output from a motor in the at least one motion generating mechanism to counteract a torque of gravity resulting from the tilt motion.

11. The non-transitory machine readable storage medium of claim 8, wherein measuring the tremor motion and the tilt motion of the handheld device includes using an accelerometer and a gyroscope included in the MTM.

12. The non-transitory machine readable storage medium of claim 11, wherein in response to measuring the tilt motion with the accelerometer and the gyroscope, a motor in the at least one motion generating mechanism produces a torque equal and opposite to a gravitational vector.

13. A handheld tool, comprising:
a housing;
at least one motion generating mechanism disposed within the housing;
an attachment arm coupled to the at least one motion generating mechanism;
a motion tracking module ("MTM") disposed in the housing to detect motion of the housing; and
a controller electrically coupled to the MTM, wherein the controller includes logic that when executed by the controller causes the handheld tool to perform operations including:
in response to the MTM detecting a tremor motion, controlling the at least one motion generating mechanism to move the attachment arm relative to the housing to reduce the tremor motion in the attachment arm; and
in response to the MTM detecting a tilt motion about a pivot point, controlling the at least one motion generating mechanism to resist the attachment arm hitting a hard stop programed into or identified by the handheld device, wherein the hard stop is an outermost point in a range of portion of the attachment arm, wherein a resistance, created by the at least one motion generating mechanism, to the attachment arm increases as the attachment arm approaches the hardstop.

14. The handheld tool of claim 13, wherein the MTM includes an accelerometer to measure high frequency motion corresponding to the tremor motion and low frequency motion corresponding to the tilt motion, wherein the controller further includes logic that when executed by the controller causes the handheld tool to perform operations including:

applying at least one of a low pass filter or a high pass filter to distinguish between the tremor motion and the tilt motion; and sending instructions to the at least one motion generating mechanism to oppose the low frequency motion and resist the attachment arm hitting the hard stop.

15. The handheld tool of claim 14, wherein the at least one motion generating mechanism includes a motor, and wherein the controller includes logic that when executed by the controller causes the handheld tool to perform operations including:

reducing the tremor motion in the attachment arm by adjusting the motor output to counteract an inertia of the housing, and resisting the attachment arm hitting the hard stop by adjusting the motor output to counteract a torque of gravity resulting from the tilt motion.

16. The handheld tool of claim 13, wherein the MTM includes an accelerometer and a gyroscope, wherein the accelerometer and the gyroscope detect an orientation of the handheld tool including a pitch of the handheld tool and a roll of the handheld tool to resist the attachment arm hitting the hard stop.

17. The handheld tool of claim 16, wherein the controller includes logic that when executed by the controller causes the handheld tool to perform operations including:

using at least one of a Kalman filter or a complementary filter to reduce the tremor motion in the attachment arm and resist the attachment arm hitting the hard stop.

18. The handheld tool of claim 16, wherein the at least one motion generating mechanism includes a motor, and wherein the controller includes logic that when executed by the controller causes the handheld tool to perform operations including:

in response to detecting the tilt motion, instructing the motor to produce torque equal and opposite to a gravitational vector to resist the attachment arm hitting the hard stop.

19. The handheld tool of claim 13, wherein the MTM includes at least one gyroscope, and the at least one gyroscope is located in at least one of a distal end of attachment arm or in the housing.

20. The handheld tool of claim 13, wherein the attachment arm is configured to receive at least one of a fork attachment, a toothbrush attachment, or a paintbrush attachment.

21. The method of claim 1, wherein the resistance to the attachment arm hitting the hard stop increases gradually prior to the attachment arm reaching the hard stop.

22. The method of claim 1, wherein the at least one motion generating mechanism is configured to apply a different hard stop resistance profile for each of a plurality of different types of attachments that removeable attach to the attachment arm.

23. The method of claim 1, wherein the hard stop is physically defined by the handheld tool.

* * * * *

UNITED STATES PATENT AND TRADEMARK OFFICE
CERTIFICATE OF CORRECTION

PATENT NO. : 10,583,061 B2  
APPLICATION NO. : 15/257111  
DATED : March 10, 2020  
INVENTOR(S) : A. Pathak et al.

Page 1 of 1

It is certified that error appears in the above-identified patent and that said Letters Patent is hereby corrected as shown below:

In the Claims

| Column | Line | |
|---|---|---|
| 9 | 16 | Please change "hard-" to -- hard --. |
| 10 | 10 | Please change "hardstop" to -- hard stop --. |
| 10 | 58 | Please change "programed" to -- programmed --. |
| 10 | 63 | Please change "hardstop" to -- hard stop --. |
| 12 | 15 | Please change "attachment" to -- the attachment --. |

Signed and Sealed this  
Eighth Day of June, 2021

Drew Hirshfeld  
*Performing the Functions and Duties of the*  
*Under Secretary of Commerce for Intellectual Property and*  
*Director of the United States Patent and Trademark Office*